United States Patent [19]
Wilkins

[11] Patent Number: 5,850,425
[45] Date of Patent: Dec. 15, 1998

[54] X-RAY OPTICS, ESPECIALLY FOR PHASE CONTRAST

[75] Inventor: Stephen W. Wilkins, Blackburn, Australia

[73] Assignee: Commonwealth Scientific and Industrial Research Organisation, Campbell, Australia

[21] Appl. No.: 845,211

[22] Filed: Apr. 21, 1997

Related U.S. Application Data

[62] Division of Ser. No. 596,188, filed as PCT/AU94/00480 Aug. 16, 1994 published as WO95/05725 Feb. 23, 1995.

[30] Foreign Application Priority Data

| Aug. 16, 1993 | [AU] | Australia | 0583/93 |
| Sep. 29, 1993 | [AU] | Australia | 1519/93 |
| Oct. 4, 1993 | [AU] | Australia | 1597/93 |
| Mar. 8, 1994 | [AU] | Australia | 4298/94 |

[51] Int. Cl.$^6$ .................................................. G21K 1/06
[52] U.S. Cl. ........................... 378/85; 378/71; 250/390.09
[58] Field of Search ................ 250/390.01, 390.02, 250/390.09, 390.1; 378/70, 71, 84, 85

[56] References Cited

U.S. PATENT DOCUMENTS

| 3,588,509 | 6/1971 | Yanagishita et al. | 250/505.1 |
| 3,869,615 | 3/1975 | Hoover et al. | 256/508 |
| 4,090,073 | 5/1978 | De Villiers et al. | 378/71 |
| 4,677,681 | 6/1987 | Klausz | 382/6 |
| 4,969,176 | 11/1990 | Marinus | 378/149 |
| 5,016,267 | 5/1991 | Wilkins | 378/84 |
| 5,245,648 | 9/1993 | Kinney et al. | 378/43 |

FOREIGN PATENT DOCUMENTS

| 1402871 | 11/1986 | U.S.S.R. |
| 2137453 | 10/1984 | United Kingdom |
| 2203620 | 10/1988 | United Kingdom |
| WO88/08530 | 11/1988 | WIPO |
| WO92/21016 | 11/1992 | WIPO |

OTHER PUBLICATIONS

Fillard et al, "Computer Simulation of Super–Resolution Point Source Image Detection", Optical Engineering, Nov. 1993, vol. 32, No. 11, pp. 2936–2944.

Bonse et al, "High Resolution Tomography With Chemical Specificity", Nuclear Instruments and Methods in Physics Research A246 (1986), pp. 644–648 No Month.

*Primary Examiner*—David P. Porta
*Assistant Examiner*—David Vernon Bruce
*Attorney, Agent, or Firm*—Nixon & Vanderhye P.C.

[57] ABSTRACT

An x-ray or neutron optic configuration includes a plurality of single crystal portions formed with respective spaced x-ray or neutron reflection faces formed at predetermined asymmetry angles to a Bragg diffraction plane in the respective crystal portion. The crystal portions are interconnected to maintain a first and second of these faces spaced apart for receipt of a sample between them and to allow small adjustments of the relative angle of the faces about the normal to the plane of diffraction while maintaining the normals to the Bragg planes for the first and second faces substantially in the plane of diffraction. A first face is arranged to be a monochromator and collimator with respect to x-rays or neutrons of appropriate wavelength incident reflected through the sample for receipt by the second face, which thereby serves as analyzer face.

21 Claims, 12 Drawing Sheets

Area ⇨ absorption contrast position

Shift ⇨ phase contrast information position width ⇨ phase contrast and homogeneity information position

X-RAY OPTICS, ESPECIALLY FOR PHASE CONTRAST

RELATED APPLICATION

This application is a division of my parent application Ser. No. 08/596,188, filed as PCT/AU94/00480 Aug. 16, 1994 published as WO95/05725 Feb. 23, 1995 (now allowed).

FIELD OF THE INVENTION

This invention relates generally in one aspect to x-ray optics and in particular to x-ray optics configurations and to a method of x-ray imaging or radiography. In another aspect, the invention also relates to a corresponding neutron beam analysis configuration.

BACKGROUND ART

Conventional x-ray radiography uses very simple optics usually consisting of a small source and possibly some geometrical defining slits and collimators.

One of the principal limitations on the obtaining of high resolution, high contrast images in conventional radiography is the problem of sample and air scatter, leading to additional background and blurring of images. This scatter is alleviated in some cases by adopting the technique of contact radiography, in which the imaging medium is placed in direct contact with the sample. The technique, however, achieves no direct magnification and is only effective for thin samples. In other cases some form of (so called "focusing") collimator may be placed between the sample and the detecting medium, as for example in some methods for recording chest x-ray radiographs.

Another limitation of conventional radiography is the problem of polychromaticity and the effect of beam hardening in a sample leading to difficulties in quantitative interpretation of radiographs.

On the other hand, a wide variety of very high-resolution x-ray optical devices have been developed for x-ray scientific applications such as the imaging of defects in semiconductor crystals, the measurement of small-angle scattering, and certain types of x-ray tomography. See for example Hashizume & Matsushita (1983) in Handbook on Synchrotron Radiation, Vol. 1, Chap. 4, pp 303–307, ed E. E. Koch, North Holland.

These techniques enable very precise definition of wavelength and collimation of both the incident radiation on the sample and also the radiation passed by the analyser. Typically in these cases the key x-ray optical elements such as the monochromator and analyser crystal are separate devices and require very high-precision independent goniometers to control the angular setting. It would be useful if reliance on such high precision components could be reduced.

Two Russian groups have recently proposed (for example, Soviet patent 1402871 and international patent publication WO92/21016 [PCT/RU92/00105])a potentially revolutionary new x-ray analytic method called refractometry or phase contrast imaging. This method is especially suitable for imaging weak absorption contrast features such as capillaries and arteries in vivo without the need for injecting a contrast medium (i.e. it is non-invasive). The technique entails irradiation of the sample by an x-ray beam which has been monochromated and collimated by Bragg diffraction from a first single crystal. The transmitted signal is then received after passing through the sample, by a second single crystal.

The arrangement disclosed in SU 1402871 by Mitrofanov et al involves two perfect crystals set at the exact matching Bragg condition with the angular collimation of the beam from the first crystal less than the range of angles of refraction from the sample, while the angular acceptance of the second crystal is also less than the angular range of refraction from the sample. The method essentially corresponds to "bright field" refractometry or phase contrast imaging. The proposal described in WO92/21016 by Belyaevskaya et al (English language counterpart U.S. Pat. No. 5,319,694) involves production of a pseudoplane wave by a first crystal before the sample such that the divergence in the plane of diffraction of the beam from the first crystal is less than half that of the acceptance range of a second crystal after the sample, and allows for fine tuning of the second crystal in order to enhance the contrast of selected features.

This new technique, in theory, can detect very fine angular path deviations, or equivalently x-ray phase shifts, but in many cases would be difficult to practicably implement with current monochromator/analysis configurations. In simple terms, x-ray refractometry i.e. imaging is the x-ray analogue of optical phase contrast microscopy and is, in principle, capable of yielding contrast from only very slight variations in x-ray optical density of a material rather than conventional absorption-contrast, which relates to the imaginary part of the x-ray refractive index. Immediate applications lie in materials science: to the study of fibre composites and ceramics, and to biological samples, eg in taxonomy.

Application of the technique to larger samples such as the human chest would require very large integrated x-ray optical devices or very precise goniometry. The successful implementation of refractometry in clinical radiography could provide a major breakthrough in cardiovascular diagnostic techniques and particularly angiography. At present, x-ray angiography is invasive in that a contrast medium must be injected. Generally, little contrast can be observed in the radiography of untreated biological tissues with x-rays, except with special measures such as the use of soft x-rays, in which case one requires very thin specimens, very long wavelength (e.g. 20 to 50 Angstrom), and a vacuum environment. These requirements are in many instances entirely inappropriate for practical purposes.

Applicant's prior U.S. Pat. No. 5,016,267 discloses a channel-cut monochromator formed in a perfect crystal or near-perfect crystal body. The channel is formed with lateral faces which multiply reflect by Bragg diffraction from selected Bragg planes. The surfaces are at an angle to each other so as to monochromatise and spatially condense the beam without substantial loss of reflectivity or transmitted power. In one embodiment, the beam is multiply reflected from closely spaced parallel faces defining a slot.

In discussions of refractometry it is important to distinguish two aspects of coherence of the illuminating radiation on the sample, namely longitudinal (temporal, wavelength dispersion) and lateral (spatial) coherence. The former relates essentially to the wavelength purity of the radiation and the latter relates essentially to the angular divergence of the radiation at a point which in turn relates to source size, collimation, position and degree of coherence of the source (see eg the text Hariharan, "Optical Interferometry", Academic Press Australia, 1985; and Ishikawa, Acta Cryst A44, 496–9 (1988)). All of hitherto approaches which have been proposed for refractometric or phase contrast imaging of x-rays and neutrons appear to rely on the assumption of a high degree of longitudinal coherence (or wavelength purity) of the penetrating radiation incident on the sample.

DISCLOSURE OF THE INVENTION

It is one object of a first aspect of the invention to provide an optical configuration which is adaptable to enhance the practical utility of the x-ray refractometry or phase contrast technique.

It is another object of this first aspect of the invention to provide an x-ray optical device adaptable to provide a significant improvement in the quality of conventional x-ray and neutron radiographs and tomographs.

It is an object of a second aspect of the invention, at least in one or more preferred embodiments, to provide for refractometric imaging in which the accurate definition of wavelength is not crucial to the formation of good quality refractometric images.

The invention accordingly provides, in its first aspect, an x-ray or neutron beam optic configuration comprising:

a plurality of single crystal portions formed with respective spaced x-ray or neutron reflection faces formed at predetermined asymmetry angles to a Bragg diffraction plane in the respective crystal portion;

means to mount a sample between a first and a second of said faces, which first face is arranged to be a monochromator and collimator with respect to x-rays or neutrons of appropriate wavelength incident on said first face and reflected thereby through the sample for receipt by the second face, said second face thereby serving as an analyzer face; and means interconnecting said crystal portions whereby to allow small adjustments of the relative angle of said faces about the normal to the plane of diffraction while maintaining the normals to the Bragg planes for said first and second faces substantially in the plane of diffraction.

In its first aspect, the invention also provides an x-ray or neutron optic configuration comprising:

a plurality of single crystal portions formed with respective spaced x-ray or neutron reflection faces formed at predetermined asymmetry angles to a Bragg diffraction plane in the respective crystal portion; and means interconnecting said crystal portions whereby to maintain a first and second of said faces spaced apart for receipt of a sample therebetween and to allow small adjustments of the relative angle of said faces about the normal to the plane of diffraction while maintaining the normals to the Bragg planes for said first and second faces substantially in the plane of diffraction.

Preferably, said interconnecting means allows maintenance and/or selection of the angular setting of the second face to be such as to help enhance contrast of desired features in x-ray images thus obtained.

In its first aspect, the invention further provides a method of deriving an x-ray or neutron beam image of a sample comprising directing an x-ray or neutron beam onto a first x-ray or neutron reflection face for reflection from that face through the sample to a second x-ray or neutron reflection face and thence to x-ray detection means, said reflection faces being interconnected such that a beam Bragg diffracted by the first face is at or near the correct angle for Bragg diffraction by the second face, said reflection faces being formed in respective single crystal portions at predetermined asymmetry angles to a Bragg diffraction plane in the respective crystal portion. In embodiments aimed at high contrast, preferably the angular and preferably also wavelength bandpass acceptance of the second face is well matched to the angular divergence and wavelength bandpass of the first face. In embodiments aimed at high spatial resolution, the angular acceptance of the second or analyses face is chosen to be larger than the angular spread of the beam leaving the first or monochromator face and corresponds to the case of Belyaevakaya et al.

An advantageous configuration for achieving high contrast images in many cases is where the two faces are well matched or where the angle of acceptance for Bragg reflection at the second face is less than the angular divergence from the first face. The term "well matched" here means that the angular divergence of the beam from the first face is approximately equal to the angular acceptance for reflection from or through the second face.

The invention further provides, in its first aspect, an x-ray or neutron optic configuration comprising:

a plurality of single crystal portions formed with respective spaced x-ray or neutron reflection faces formed at predetermined asymmetry angles to a Bragg diffraction plane in the respective crystal portion; and means to allow small adjustments of the relative angle of said faces about the normal to the plane of diffraction while maintaining the normals to the Bragg planes for said first and second faces substantially in the plane of diffraction;

wherein said means allows maintenance and/or selection of an angular setting of the second face which is well matched in angular acceptance to the angular divergence of the beam from the first face, or is of higher angular resolution.

The first aspect of the invention moreover provides a method of deriving an x-ray or neutron beam image signal of a sample comprising directing an x-ray or neutron beam onto a first x-ray or neutron reflection face for reflection from that face through the sample to a second x-ray or neutron reflection face and thence to x-ray detection means, said reflection faces being formed in respective single crystal portions at predetermined asymmetry angles to a Bragg diffraction plane in the respective crystal portion, and further including maintaining and/or selecting an angular setting of the second face which is well matched in angular acceptance to the angular divergence of the beam from the first face, or is of higher angular resolution.

If the angular acceptance at the second face is chosen so as to be less than the divergence of the beam due to refraction in the sample the configuration can be utilised in a refractometric mode. If the angular acceptance of the second face is of the order of or larger than such divergence of the beam, the configuration operates either in a high spatial resolution phase or in a conventional absorption contrast mode depending on the coherence of the illuminating radiation on the sample.

In some applications, eg contrast mode or "bright field" configurations, it is advantageous to choose the aforementioned asymmetry angles so as to have both the angular and wavelength acceptance bandpass of the second face for the radiation well matched to the angular and wavelength reflection bandpass of the first face.

The single crystal portions may be segments of a monolithic perfect or near-perfect single crystal shaped by initial growth or subsequent modification to define the respective reflection faces. In this case, the interconnecting means is the crystal itself and the reflection faces are formed at predetermined asymmetry angles to a common Bragg diffraction plane in the crystal. Alternatively, the single crystal portions may be discrete crystals, possibly cut from an original common crystal, secured for example to a base or frame which comprises the interconnecting means.

Preferably, the interconnecting means may be adapted to effect fine tuning and/or detuning of the relative angles of said first and second faces. Such means may also serve to compensate for the effect of refractive index variation with asymmetry angle. The fine tuning means may include means for effecting fine adjustment of the relative angles between the faces, eg by flexing segments of a single crystal, or segments of a base or frame comprising the interconnecting means. The angular range of tuning capability is preferably at least ±20 seconds of angle, at least for low energy applications (of order 8 KeV, say). Angular resolution is preferably at least ±0.1 sec, more preferably ±0.05 or even ±0.01 second of angle, especially for high energy medical applications. The fine tuning means may further involve associated fine adjustment positional transducers such as linearly adjustable threaded devices, piezoelectric crystals or small electromagnets. An alternative means for effecting fine tuning and/or detuning may be the use of the refraction effect via the insertion of appropriately shaped plates.

Advantageously, the first aspect of the invention is particularly applied to x-ray imaging. The apparatus preferably includes an imaging detector, most preferably a two-dimensional imaging detector.

The configuration preferably further includes a source of x-ray radiation arranged to direct a beam of x-rays onto said first face, which source typically includes means to restrict the cross-section of the beam and to enhance the angular collimation and intensity of the beam.

Preferably, said first face exhibits an angular collimation and said second face exhibits a matching angular acceptance which in the case of refractometry is chosen so as to be less than to the angular divergence of the beam coming from the sample due to refraction. In the case of conventional radiography or tomography, the angular width of acceptance of the second face will be equal to, or larger by a small factor than, the intrinsic divergence due to refraction in the sample, so as to integrate most of the contrast variation due to refractive index variations in the sample.

The second face may demagnify the beam laterally in the plane of diffraction and it is therefore preferable to provide a third or further x-ray reflection faces, eg in the perfect or near perfect single crystal, so as to enhance contrast and/or to magnify the beam for receipt by the detection means or in other cases to simply magnify the beam to match the radiation of the optics to the detector means.

Conveniently, the monolithic crystal may be cut to provide a base and integral upstanding lands, e.g. pillars, providing the respective x-ray reflection faces.

Preferably, where faces are required to be "substantially parallel", the tolerance from exact parallelism is no greater than of the order of 0.5° but exact magnitude will depend on the degree of asymmetry and wavelength.

It is emphasised that the x-ray optics of the first aspect of the invention may be used for conventional absorption contrast imaging or radiography as well as the phase contrast applications described in detail herein. Indeed it is envisaged that a multi-purpose highly flexible instrument would be provided, adaptable to a variety of both absorption contrast and phase contrast applications.

In its second aspect, the invention still further provides a method of imaging of an object, which method includes irradiating the object with radiation from a source so that in the object the radiation is substantially or highly laterally coherent or nearly so, and detecting one or more sub-beams of said radiation after they have passed through the object, wherein the transverse location of said sub-beam(s) of said radiation is detected at said detector and said radiation is intercepted by one or more means each defining one or more apertures which form said sub-beam(s), which apertures are sufficiently small with respect to the relative location of said source and detector (i) for said transverse location to be sensitive to refractive angular deviation of the radiation by the object, whereby to provide information about a constituent of the object causing said deviation; and/or (ii) for said detected sub-beams to be sufficiently resolved and contrasted with respect to background to provide information about a constituent of the object causing partial or complete absorption of one or more sub-beams.

In its second aspect, the invention also provides apparatus for imaging of an object, including:
a source of radiation,
a detector for the radiation sufficiently spaced from the source for radiation from the source to be substantially or highly laterally coherent or nearly so in an object when such is disposed for irradiation by the radiation and detection thereafter by the detector;
wherein the detector is configured for detection of the transverse location of one or more sub-beam(s) of the radiations, and there is further provided one or more means each defining one or more apertures for forming said sub-beam(s), which apertures are sufficiently small with respect to the relative location in use of said source and detector (i) for said transverse location to be sensitive to refractive angular deviation of the radiation by the object, whereby to provide information about a constituent of the object causing said deviation; and/or (ii) for said detected sub-beams to be sufficiently resolved and contrasted with respect to background to provide information about a constituent of the object causing partial or complete absorption of one or more sub-beams.

The means defining one or more apertures may be arranged to be between the source and object, or between the object and detector, or both, or may be provided in combination with the detector. For example, in the latter case, a detector comprising a pixellated two-dimensional planar array, eg a charge-coupled diode (CCD) array or the like, may itself be considered to act as a set of apertures combined with detector since each pixel has a border. Moreover, signal data recorded for individual pixels may be ignored in stages of data processing thus leading to an effective pattern of apertures in front of the detector.

In a preferred embodiment of the second aspect of the invention, the means defining one or more apertures is arranged to be disposed between the source and the object and preferably comprises screen means blocking the radiation save for a plurality of spaced microapertures, eg of mean width in the range 0.1 to 50 micron, most preferably 1 to 20 micron, spaced apart sufficiently for the sub-beams passed to the object and detector to be spaced apart at the detector to a degree consistent with the refractometric angular deviation of interest and the spatial resolution of the detector. The microapertures are preferably arranged in a regular array at centre-to-centre spacings preferably greater than twice their widths, eg three to four times their widths.

In the second aspect of the invention, the source is preferably a spot source of diameter of similar order to the microapertures, eg around 10 micron. The displacement of the screen means, and in use the object, from the source is preferably such that the radiation is effectively substantially parallel at the microapertures and object. This displacement may be, for example, at least 0.5 m, preferably in the range 1 to 5 m.

The detector for the second aspect of the invention is preferably a pixellated two-dimensional planar array, eg a charge-coupled diode (CCD) array or the like. The pixel size is preferably consistent with the geometry of the apparatus including the microaperture sizes, sub-beam size and refractometric angular shift for the desired degree of resolution, but may conveniently be for example an array of square pixels of width in the range 5 to 50 micron. In this context, "substantially or highly laterally coherent" preferably indicates that lateral coherence is such that intensity peaks at the detector due to individual sub-beams span several pixels (eg 3 to 5 in each orthogonal direction) but not so broad that neighbouring peaks have substantial overlap after allowing for possible refraction effects. In general, for approximately point sources, the smaller the source size the higher the lateral coherence while for highly parallel illumination from an extended source, the more nearly parallel the beam the greater the lateral coherence.

The radiation in the second aspect of the invention is preferably x-ray radiation and may be monochromatic or polychromatic, even broad-band polychromatic. The apparatus is preferably arranged to provide uniform 2-dimensional magnification. The detector preferably exhibits high positional stability in its readout.

The invention in both of its aspects is especially useful with hard x-rays, i.e. radiation greater than 5 keV.

BRIEF DESCRIPTION OF THE DRAWINGS

The invention will be further described, by way of example only, with reference to the accompanying drawings, in which.

EMBODIMENTS OF THE INVENTION

Figure 1:
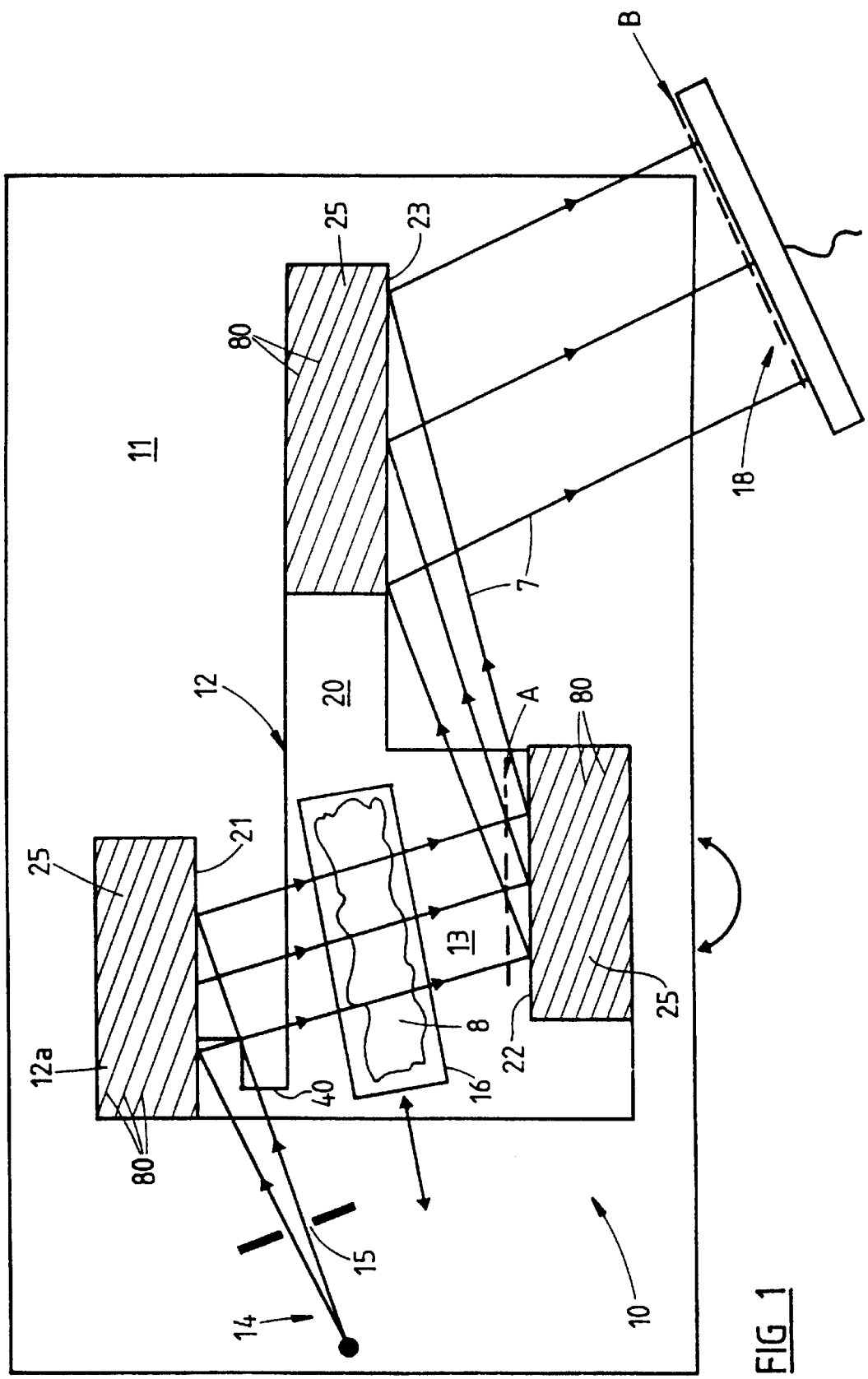
FIG. 1 is a diagrammatic plan view of a simple x-ray optics configuration in accordance with an embodiment the first aspect of the invention.

The simple x-ray optics configuration 10 depicted in FIG. 1 includes a monolithic perfect or near-perfect single crystal 12 of synthetically grown silicon, of the type used for example in the semi-conductor industry. Further components are an x-ray source 14 including a defining slit 15, a movable sample stage 16, and a detector 18. The detector may be a high spatial resolution x-ray film or wide dynamic range photostimulable storage phosphor imaging plate. Alternatively, electronic imaging detectors such as those based on charge coupled devices (CCD's) may be used for high speed and, in some cases, real time recording of images.

Crystal 12 is supported atop a flat base 11, to which it is secured (for reasons which will become apparent) only in the region of crystal corner 12a. X-ray source 14, sample stage 16 and detector 18 are also secured with respect to base 11, by any suitable means well known in the art and dependent on the exact nature of the component. Sample stage 16 will normally traverse from above or to the side of crystal 12.

Figure 2:
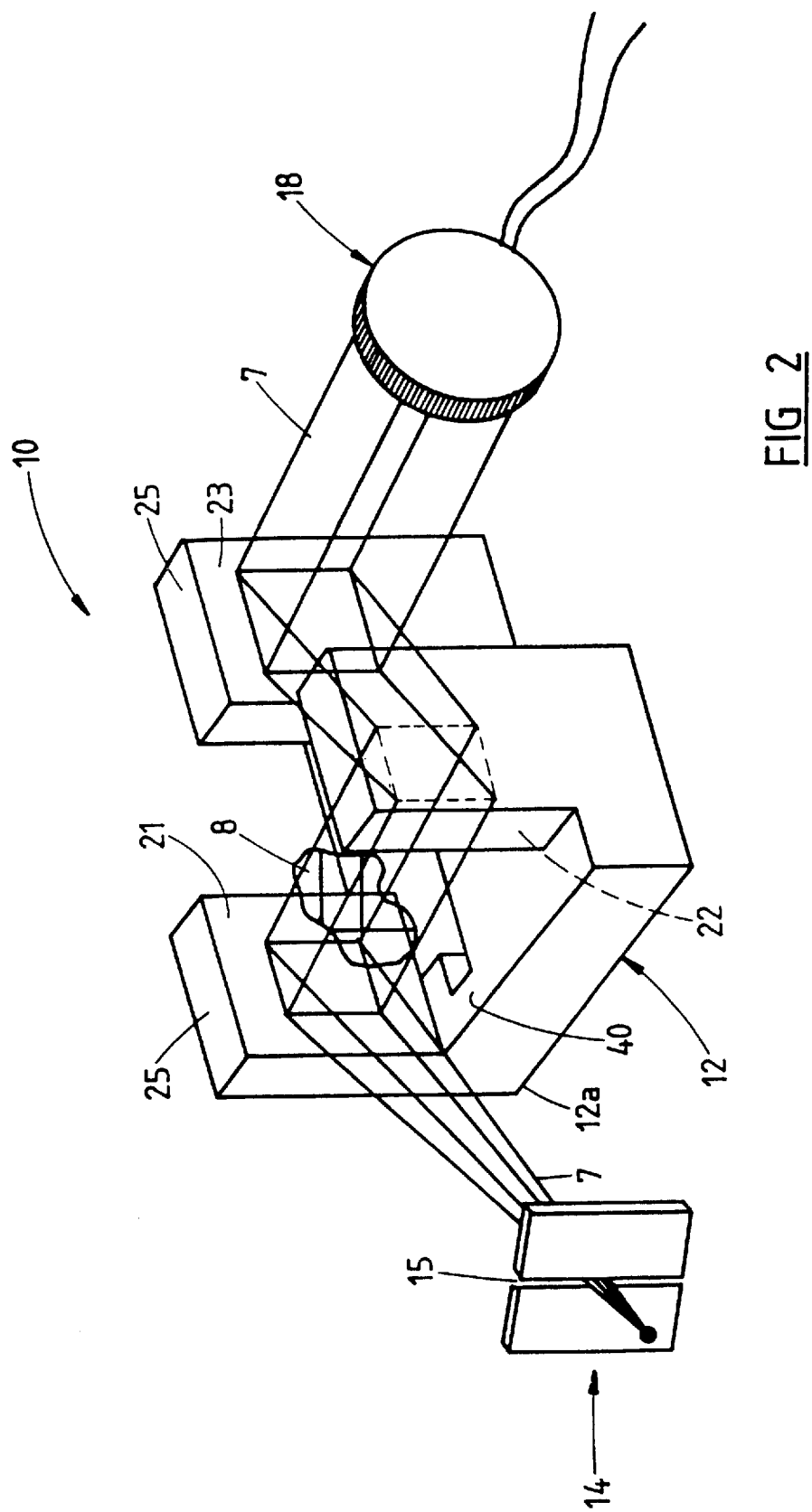
FIG. 2 is a diagrammatic isometric view of the configuration shown in FIG. 1.

Crystal 12 includes a generally L-shaped base 20 and three upstanding lands or pillars 25 of generally rectangular cross-section. Pillars 25 are arranged at respective corners of the crystal as illustrated and define three substantially parallel x-ray reflection faces 21,22,23 formed at predetermined asymmetry angles to a common set of Bragg diffraction planes in the crystal. These planes are of course not visible but are represented by lines 80 in FIG. 1. It will be seen that the arrangement is such that the x-ray beam emerging from slit 15 is asymmetrically reflected and magnified from face 21 across a substantial open space 13 which receives sample stage 16 bearing its sample 8, for asymmetric demagnifying reflection from face 22 and then an inverting magnifying reflection from face 23 to detector 18. Face 21 is a collimating face and is also wavelength sensitive and therefore serves as a monochromator face in the usual manner. By appropriate choice of the asymmetry angle at face 21, both the lateral collimation and lateral extent of the x-ray beam can be greatly enhanced. The ray lines 7 drawn in FIGS. 1 and 2 are not intended to be accurate or scaled representations of the beam but are merely intended to be indicative of its course from the source to the detector. For example, each reflection alters the angular divergence of the beam. Angular acceptance for a given pure wavelength of CuKα radiation from a point source is of the order of 10 arcseconds when incident on face 21 and for the demagnified beam incident on face 23, and of the order of 1 arcsecond in the more magnified portions of the beam incident on face 22.

The angular and wavelength reflection bandpasses of the faces 21,22 are well matched, as earlier defined, whereby face 22 becomes a highly efficient discriminator against scattered radiation in the case of exact tuning of face 22 to monochromator face 21. On the other hand, when face 22 is detuned with respect to face 21, face 22 becomes extremely sensitive to any scattering effected by a sample 8 disposed between the faces on sample stage 16. It is thus possible to achieve a very high contrast with low background contamination and absence of beam hardening effects, notwithstanding a very low contrast in some cases utilising conventional x-ray imaging techniques. In this manner, face 22 serves as a high resolution analyser face.

Figure 3:
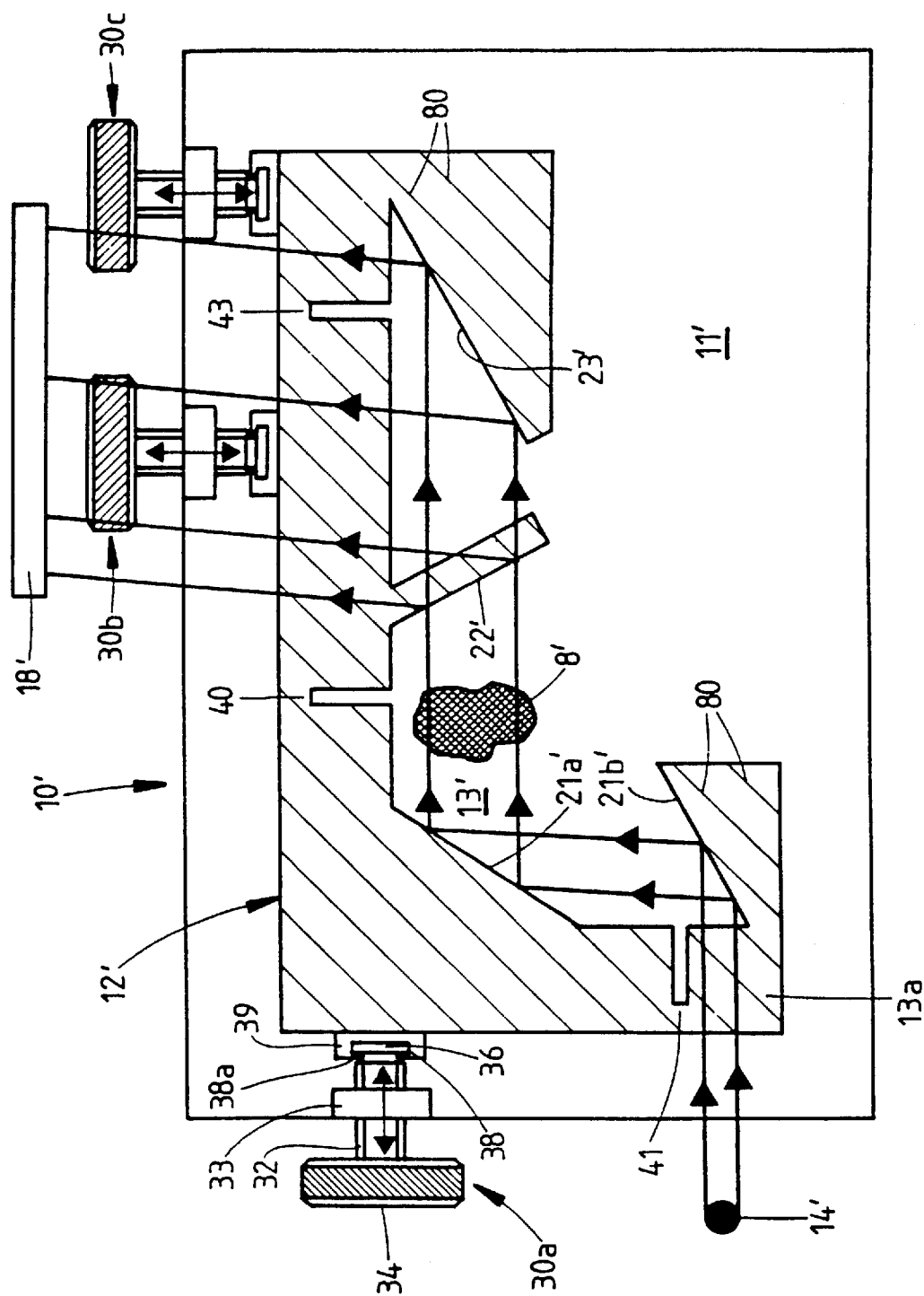
FIG. 3 is an alternative embodiment utilising a pair of monochromator faces and a different arrangement of the analyzer faces.

FIG. 3 (in which like primed reference numerals are used to indicate like features) depicts a modified embodiment in which the single crystal 12 defines a pair of monochromator/collimator faces 21a',21b', analyser face 22' and magnifying face 23'. Faces 21a',21b' are shown with a common Bragg plane but this is not necessarily so. In this case, however, the face 23' is also tuned as an analyser face, receiving and reflecting the component of the beam transmitted by analyser face 22'. Detector 18' separately receives the demagnified beam from the analyser face 22' and the magnified beam reflected by face 23'. This alternative configuration is suitable where the diffraction condition corresponds to the Laue case, where the diffracted beam passes right through the crystal element This is particularly relevant to high-energy x-ray applications.

Figure 4:
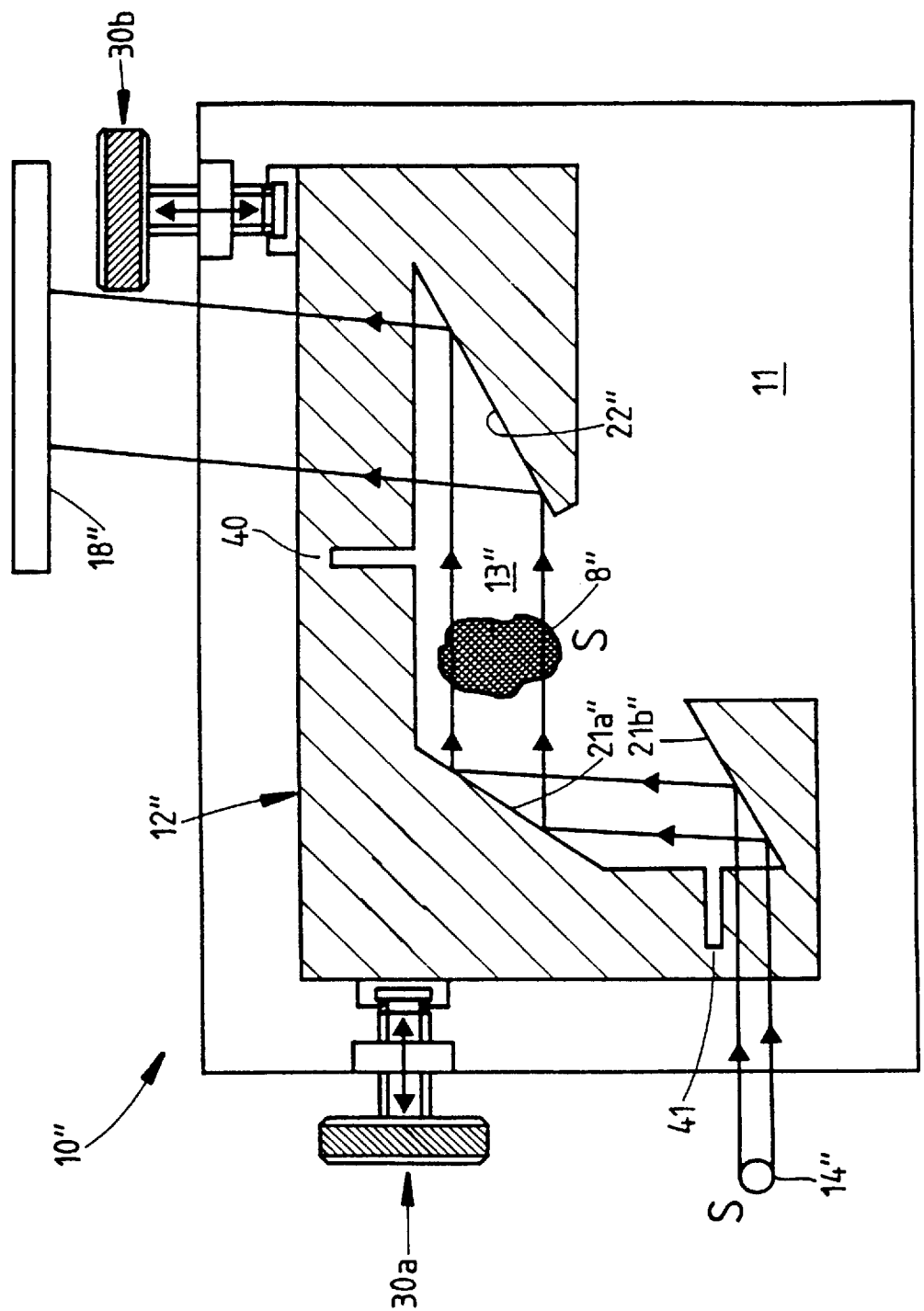
FIG. 4 is a further modification with a pair of monochromator faces but direct magnification in the plane of diffraction.

A further modification utilising a pair of monochromator faces but only a single magnifying analyzer face is depicted in FIG. 4.

Figure 5:
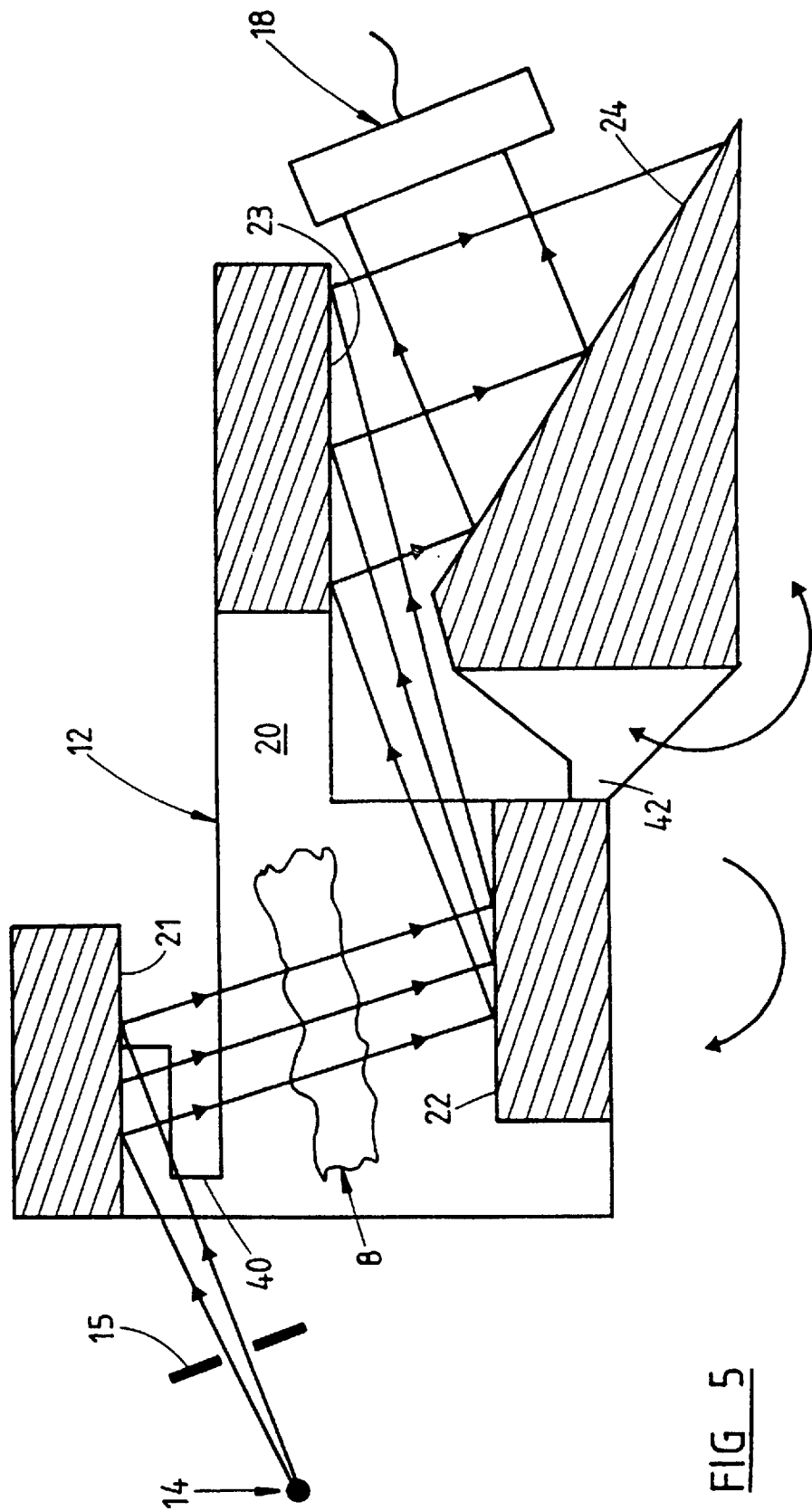
FIG. 5 is a still further modification with enhanced magnification.

FIG. 5 shows an extension of the basic three-reflection integrated optic depicted in FIGS. 1 and 2 and provides a net lateral (in plane of diffraction) magnification of the image of the sample. Some lateral magnification of the image could also be obtained in the basic three-reflection device by increasing the asymmetry angle of the face 23 in FIG. 1 relative to the other faces, but in practice the degree of asymmetry of faces 21,22,23 may already be close to the asymmetric limits where specular reflection becomes significant, and so an additional face 24 to provide lateral beam expansion and collimation, and hence lateral magnification, may become efficacious. Net magnifications of order 50 are achievable leading to spatial resolution capability of sub-micron order. Face 24 is still cut from the common crystal 12 also defining faces 21,22,23.

Correction for refractive index mismatch in Bragg conditions at different faces may be made by introduction of reduced cross-section neck or web flexures 40 (FIGS. 1, 2, 3, 4 and 5), 41 (FIGS. 3 and 4), 43 (FIG. 3) and 42 (FIG. 5) to allow fine adjustment of the relative angles of the respective pairs of faces, or by insertion of appropriate plates to introduce a compensating refraction effect. Flexures 40 permit related adjustment of monochromator face 21 and analyser face 22. Flexures 41 (FIGS. 3 and 4) and 43 (FIG. 3) respectively allow adjustment between monochromator faces 21a',21b', and between the analyser faces 22',23'. Flexure 42 in the embodiment of FIG. 5 provides for relative adjustment of the two magnifying faces 23,24.

FIGS. 3 and 4 schematically depict simple positive transducers 30a,30b,30c, for effecting the adjustments provided by flexures 40,41,43. Each transducer 30 consists of a finely threaded stud 32 mounted in a matching threaded aperture of an upstanding bracket 33 fixed to base 11'. This stud carries a knurled knob 34 at its outer end and a disc 36 at its inner end which is received in a matching socket 38 of a respective integral lug 39 on crystal 12'. Lug 39 defines an inwardly directed flange 38a for retaining disc 36. Adjustment is effected by manually rotating knob 34 to move stud 32 in or out. With corner 13a of crystal 12' fastened down, transducer 30a finely pivots the crystal at flexure 41, transducer 30b at flexure 40 and transducer 30c at flexure 43. In a practical instrument, transducers may of course be piezo driven or electromagnetically driven and be machine servo controlled, eg in a computer managed instrument.

Figure 6:
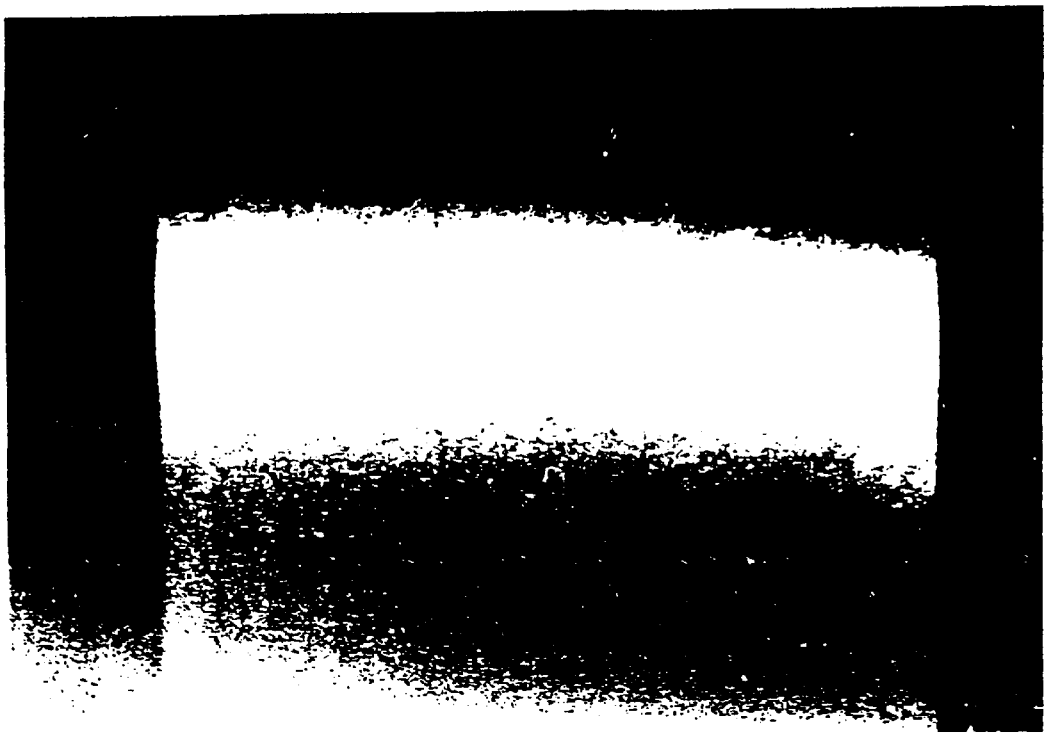
FIGS. 6 and 7 are photocopies of high-resolution radiographs of a eucalyptus leaf (eucalyptus melliodora) respectively recorded in air using x-ray dental film (including lead backing) at positions A and B in FIG. 1.
Figure 7:

FIGS. 6 and 7 are photocopies of radiographs respectively recorded with x-ray dental film (including lead backing) at positions A and B in FIG. 1, for a sample comprising a eucalyptus melliodora leaf. Position A is several millimeters after the sample and before analyser face 22 and accordingly FIG. 6 is in effect a conventional high resolution radiograph of the leaf. In the original radiograph, at best with considerable imagination, it is possible to depict some evidence of the veins of the leaf. FIG. 7, on the other hand, utilises the configuration and method of the invention and more particularly the above-mentioned refractometric technique. It will be seen that this high resolution refractometric image recorded at detector 18 is a very clear map of the leaf veins. A comparison between FIGS. 6 and 7 demonstrates the power of the inventive system applied to the practice of x-ray refractometry.

The detailed theory for calculating the properties of integrated optics of the kind envisaged by the first aspect of the invention is based on the dynamical theory of x-ray diffraction for perfect crystals (see e.g. the Hashizume & Matsushita paper referred to earlier). As an illustration of the sort of performance which is achievable by such imaging optics, we consider the case of the crystal 12, made from silicon, in the configuration of FIGS. 1 and 2 and using the 422 reflection as the operating Bragg diffraction planes and CuKα radiation from a conventional x-ray tube source 14. In this case, the calculated performance figures are:

| Face 21 | |
| --- | --- |
| Angular divergence from face 21 | 0.8 arcsec |
| Fractional wavelength bandpass from face 21 | approx $4 \times 10^{-4}$ but depends on slit width |
| Bragg angle | 44.01° |
| Asymmetry angle | −39° |
| Spatial expansion of beam (lateral magnification) | 12 |
| Face 22 | |
| Angular divergence from face 22 | as for incident beam on face 1 |
| Fractional wavelength bandpass from face 22 | $4 \times 10^{-4}$ (approx) |
| Bragg angle | 44.01° |
| Asymmetry angle | 39° |
| Spatial expansion of beam (lateral magnification) | 0.0833 |
| Face 23 | |
| Angular divergence from face 23 | 0.8 arcsec |
| Fractional wavelength bandpass from face 23 | $4 \times 10^{-4}$ (approx) |
| Bragg angle | 44.01° |
| Asymmetry angle | 39° |
| Spatial expansion of beam (lateral magnification) | 12 |
| Combined Effect | |
| Lateral spatial resolution | 0.25 μm |
| Angular collimation of transmitted beam | 0.8 arcsec |
| Fractional wavelength bandpass | $4 \times 10^{-4}$ (approx) |
| Lateral magnification of image | 1 |

With the parameters listed above, in-plane spatial resolution at levels of micron order is theoretically possible. Moreover, blurring due to scatter in the sample and air-scattering is essentially eliminated. This is combined with the fact that the beam is monochromatic to a very high degree, with a fractional bandpass of $4 \times 10^{-4}$ so that beam hardening is non-existent. Further, intensities of images will be high for diffraction optics because all the usable signal from the sample can be analysed simultaneously and, for the configuration shown in FIGS. 1 and 2, the transmission bandpass of the primary optics is broad both in wavelength and angle leading to maximal transmitted flux through the monochromator.

In the discussion of the performance of the integrated x-ray optic configuration shown in FIGS. 1 and 2, discussion has so far only been in terms of the in-plane (lateral) resolution of the system. For the case of a point source 14 the out-of-plane resolution will be that of conventional projection radiography but with the added advantage of precisely defined wavelength and reduced scatter due to lateral collimation. That is, spatial resolution in the out-of-diffraction plane direction will principally be determined by source size in that direction. It may be noted that the optic described above can work quite effectively even with an extended (line) source in the plane of diffraction although with some reduction in spatial resolution due to a small reduction of angular collimation and associated increase in bandpass. Resolution and contrast may be improved by inserting an additional dispersively coupled monochromator.

The basic design for an integrated x-ray optical imaging device as illustrated in FIGS. 1 and 2 can be enhanced in various ways. For example, and as already discussed in connection with FIG. 5, additional magnifying elements may be constructed after face 23 to provide for greater magnification. In practice these would require some form of tilt adjustment to correct for the refractive index effect. The source 14 and slit 15 may be extended laterally in the plane of diffraction so that the divergence then becomes limited by the wavelength spread of the CuKα radiation, for example. In practice this would correspond to using a line source with the line source lying in the plane of diffraction.

The crystal elements 21,22, and 23 may be appropriately turned so as to accept a wider angular range of the CuKα radiation coming from the source.

If the angular collimation of the beam from the monochromator face 21 and the angular acceptance of the beam by the analyser face 22 when they are both aligned at the exact Bragg condition are such as to be greater than the angular deviations of the beam due to x-ray optical beam path (phase) variations in the sample, then the imaging device operates in refractometric mode and essentially in bright field phase-contrast mode (i.e. negative contrast due to refractive index variation induced intensity losses from direct beam direction). On the other hand, if the angular acceptance of the analyser face 22 is of the order of or larger than the angular deviations due to refractive index variations in the sample, then the imaging devices may operate either in a conventional absorption contrast mode, recording the attenuation of a ray in the sample due to linear absorption, or in phase contrast mode, depending on the coherence of the source. However, if the angular collimation of face 21 and the angular acceptance of faces 22,23 are both better than the angular deviation due to refractive index induced effects in the sample and the second face is detuned with respect to the Bragg condition in the absence of a sample, then entirely new types of x-ray imaging information can be obtained and the technique of dark-field refractometry or phase contrast imaging can be practised. The new information relates to variations in x-ray optical density (refractive index) variation in the sample. This technique offers new possibilities for imaging the microstructure of materials and biological samples where absorption contrast is poor. The configuration of the invention is especially suited to such an application because the monolithic construction offers the potential of high mechanical stability and simple construction, and pre-alignment or near alignment of Bragg planes.

Figure 8:
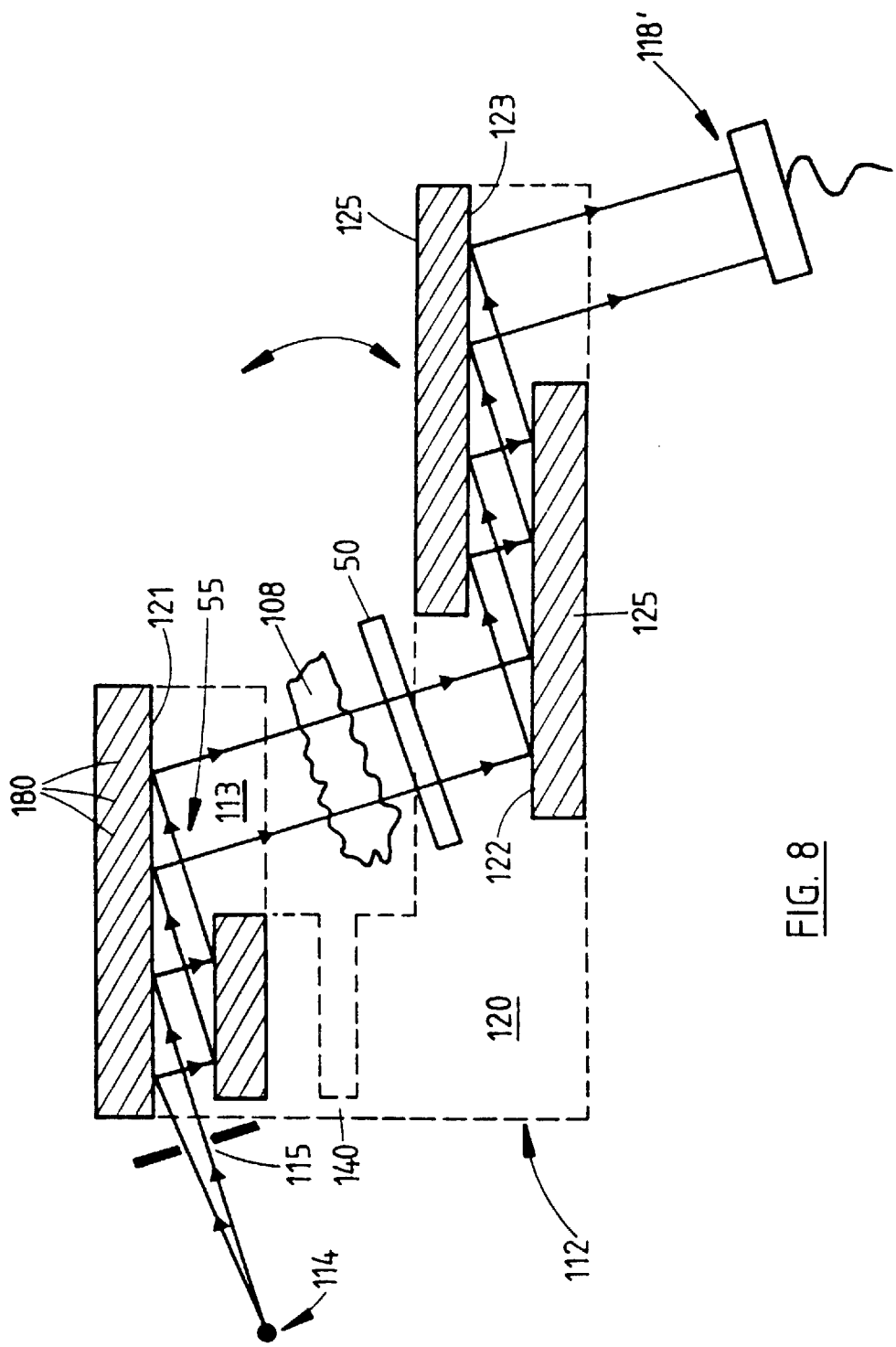
FIG. 8 is a diagram of a further embodiment of the first aspect of the invention suitable for small angle scattering imaging or ultra-high contrast refractometric imaging.

A further novel application of the present type of integrated x-ray optical devices according to the first aspect of the invention is to a technique in which x-ray scattering from a sample is imaged under conditions where there is a slight angular offset between face 21 and the combination of faces 22,23 facilitating ultra-high angular resolution refractometric or small-angle scattering imaging. An exemplary configuration is shown in FIG. 8 and includes a multiple reflection monochromator/collimator arrangement 55. In FIG. 8, like parts are indicated by like reference numerals in a "100" series. Under these conditions, the intensity in the image reflects the refractive index and small-angle scattering from the sample point-by-point at high spatial resolution and contrast. This might be used to image the distribution of particles above a certain size in a composite, or to image different components in an inhomogeneous material in which the components exhibit significantly different small-angle scattering contributions. It may be necessary to introduce a horizontal slit 50 (FIG. 8) and to record such images in one-dimensional strips to avoid overlapping-image problems, ie to improve resolution in the out-of-diffractive plane direction. FIG. 8 also depicts a flexure 140 provided in a different location to the corresponding flexure 40 of FIG. 5.

The range of potential applications of the proposed x-ray or neutron configurations and methods of the first aspect of the invention is vast. The range spans the fields of materials science, manufacturing industry, geology, biological, biomedical and clinical medicine. In the case of materials science, applications include the study of "green state ceramics", the study of composites (e.g. those used in the aerospace industry), fracture mechanics, etc. In the field of forest products, the new imaging technique offers the possibility of very high resolution and good contrast imaging and tomography of the structure of wood at the cellular level. This is relevant to the estimation of the strength and usefulness of an area of forest based on a series of small test samples of wood.

Either by development of very large monolithic or effectively monolithic monochromators or by precise mechanical goniometry, the imaging techniques described above could have relevance to clinical radiography. Another important difference between the earlier techniques and the requirements of clinical radiography are that the wavelength of the x-rays is usually much shorter. For example, for clinical radiography the wavelength may be around 0.1 Ang which means that Bragg angles for a given reflection are much smaller than, say, for CuKα and the widths of the reflectivity curves for reflection from the individual faces are much narrower, typically less than 1 arcsec. This places very stringent requirements on the precision of crystal cutting, mechanical stability and alignment of faces. In the case of refractometry, the deviation of the real part of the refractive index from unity varies roughly as wavelength to the second power and this means that the effects of x-ray optical density variation are much weaker at these short wavelengths. In addition, intense pulsed x-ray sources may be desirable in order to stop the motion of the heart in the radiograph, or to record in synchronism with the heart beat of the patient By way of explanation preliminary to describing the second aspect of the invention in detail, the nature of the x-ray refractive index of a material, and its effects, will now be reviewed. This explanation follows the treatment of the Yang, B. X. (1993) Nucl. Instrum & Meths, A328, 578–87.

The x-ray refractive index of a material may be written as $$n = 1 - \delta - i\beta$$

For elementary materials $\delta$ and $\beta$ are related to the atomic scattering factor $f = f_1 + if_2$ by the following expression $$\delta + i\beta = \frac{r_o \lambda^2}{2\pi} n_o (f_1 + if_2)$$

where $r_o$ is the classical electron radius, $\lambda$ the wavelength of the radiation and $n_o$ the number of atoms per unit volume. The well-known total photoelectric attenuation coefficient $\mu(\lambda)$ is obtained via the optical theorem $$\mu(\lambda) = \frac{4\pi\beta}{\lambda} \; 2 n_o r_o \lambda f_2$$

and is the sole source of contrast in conventional radiography. For compounds $$\delta + i\beta = r_o \frac{\lambda^2}{2\pi} n_o \sum_k (f_1{}^k + i f_2{}^k) \quad (1)$$

where k runs over all the atoms in the molecule and $n_o$ is the number of molecules per unit volume.

The equation holds generally for photon energies exceeding 1 keV except in the narrow energy region near absorption edges where some chemical effects such as EXAFS may occur. In the high energy region where the photon energy is greater than the k-shell binding energy, the photoionization cross-section monotonically decreases with increase in x-ray energy, and the scattering, especially Compton scattering, gradually dominates the photoelectric effect cross-section. Hence the atomic scattering factors of all materials approach the free-electron limit, ie $f_1 \to Z$ and $f_2 \to Zf^\circ$, where $f^\circ$ is the scattering length of a free electron.

In the x-ray region, the minute differences between indices of refraction for different materials, often of the order of $10^{-5}$ or $10^{-6}$, has led to phase-contrast (refractive) effects being ignored in conventional x-ray imaging. However, Mitrofanov et al [GB 2317453], and more recently Belyaevskaya et al [WO92/21016], have described how such effects may be used to form contrast in x-ray images using highly coherent x-rays obtained via perfect-crystal monochromator-collimators and involving Bragg diffraction of x-rays. However, as mentioned, these techniques require high temporal or longitudinal coherence and the second aspect of the present invention overcomes or at least substantially alleviates this limitation.

Figure 9:
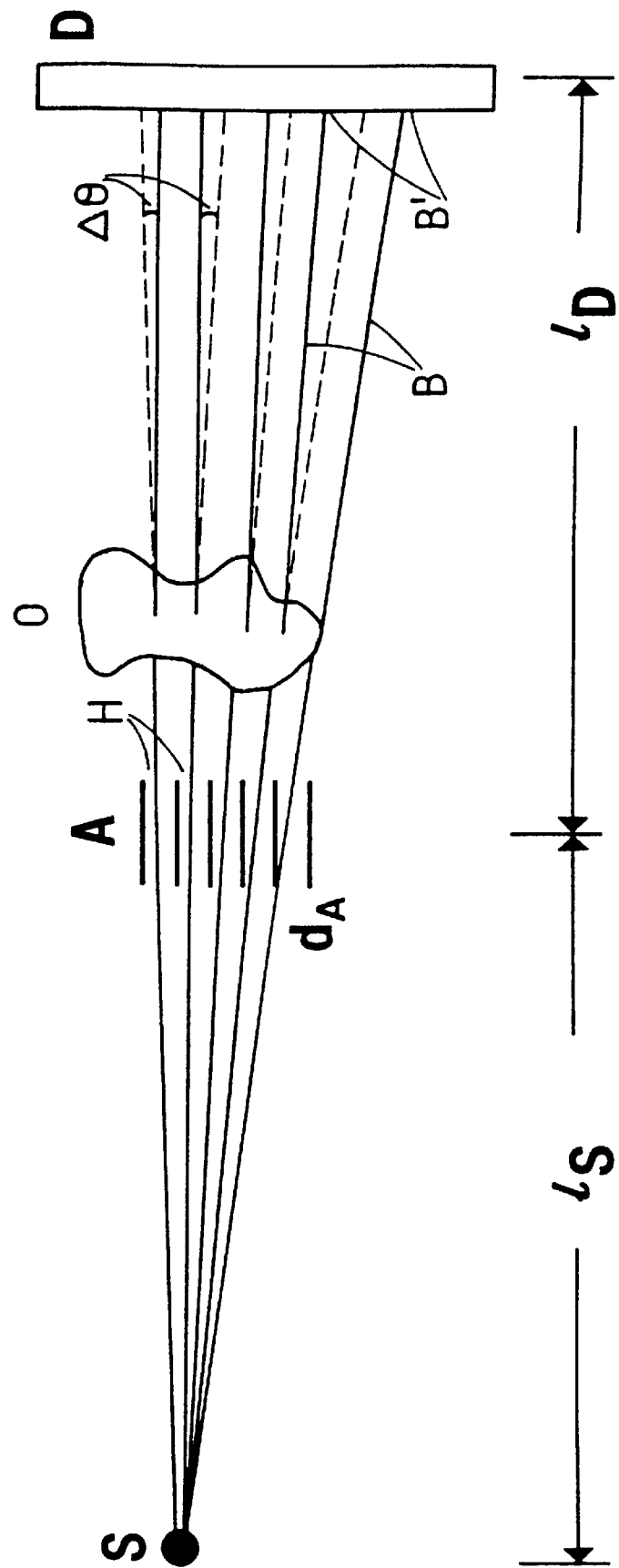
FIG. 9 is a simplified diagram of an optics configuration according to an embodiment of the second aspect of the invention.

A schematic illustration of an embodiment of the second aspect of the invention is presented in FIG. 9 and includes a high spatial coherence source such as a point source (S) which can be monochromatic but may be broadband polychromatic. Screen means (A) defining an array of microapertures (H) is placed in front of and close to the object under study (O). The spacing between microapertures (H) in the screen is chosen such that transmitted beams are spatially well separated on a 2-dimensional imaging detector (D) An example of such an array is depicted in 3-dimensional view in FIG. 10. Except at apertures (H), which pass sub-beams B, screen (A) is non-transissive or blocking to the x-rays from source (S). Detector D is a CCD or similar pixellated array having square pixels (P) of width eg 5–30 micron.

A suitable point source (S), in this case, is a high brilliance polychromatic x-ray source such as from a microfocus x-ray tube either of scientific or medical x-ray variety with, e.g. tungsten target and appropriate filters. Effective source size might typically be around 20 μm or so. Other possible sources would include quasi-parallel illumination such as at a large distance (tens of metres) from a synchrotron source.

Figure 11:
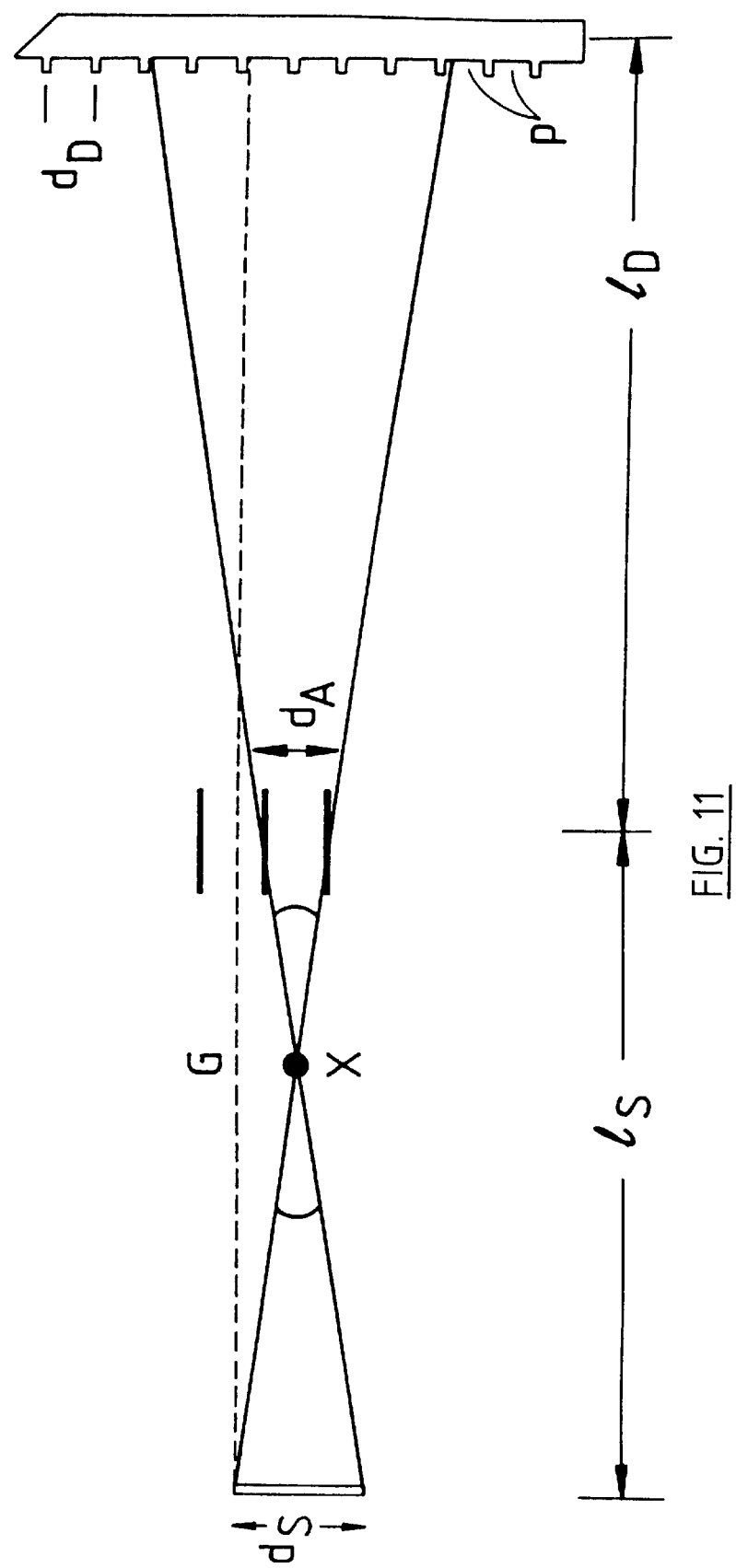
FIG. 11 is a modified form of the diagram of FIG. 9 for use in calculating parameters of the configuration.

As a first approximation, the size of spots (B') formed by sub-beams B on the detector in a given direction perpendicular to the optical axis will be given, with reference to the parameters indicated in FIG. 11, by:

$$q_D = (d_A + d_S)\left[\frac{d_A}{(d_A + d_S)} + \frac{l_D}{l_S}\right], \quad (2)$$

where $d_S$ is the source size in the given direction $d_A$ is the size of the aperture in the given direction $l_S$ is the distance between source S and microaperture array A $l_D$ is the distance between microaperture array A and detector D; and Refraction of x-rays by the sample will lead to small angular deviations, Δθ(FIG. 9), in the transmitted beam direction.

Figure 10:
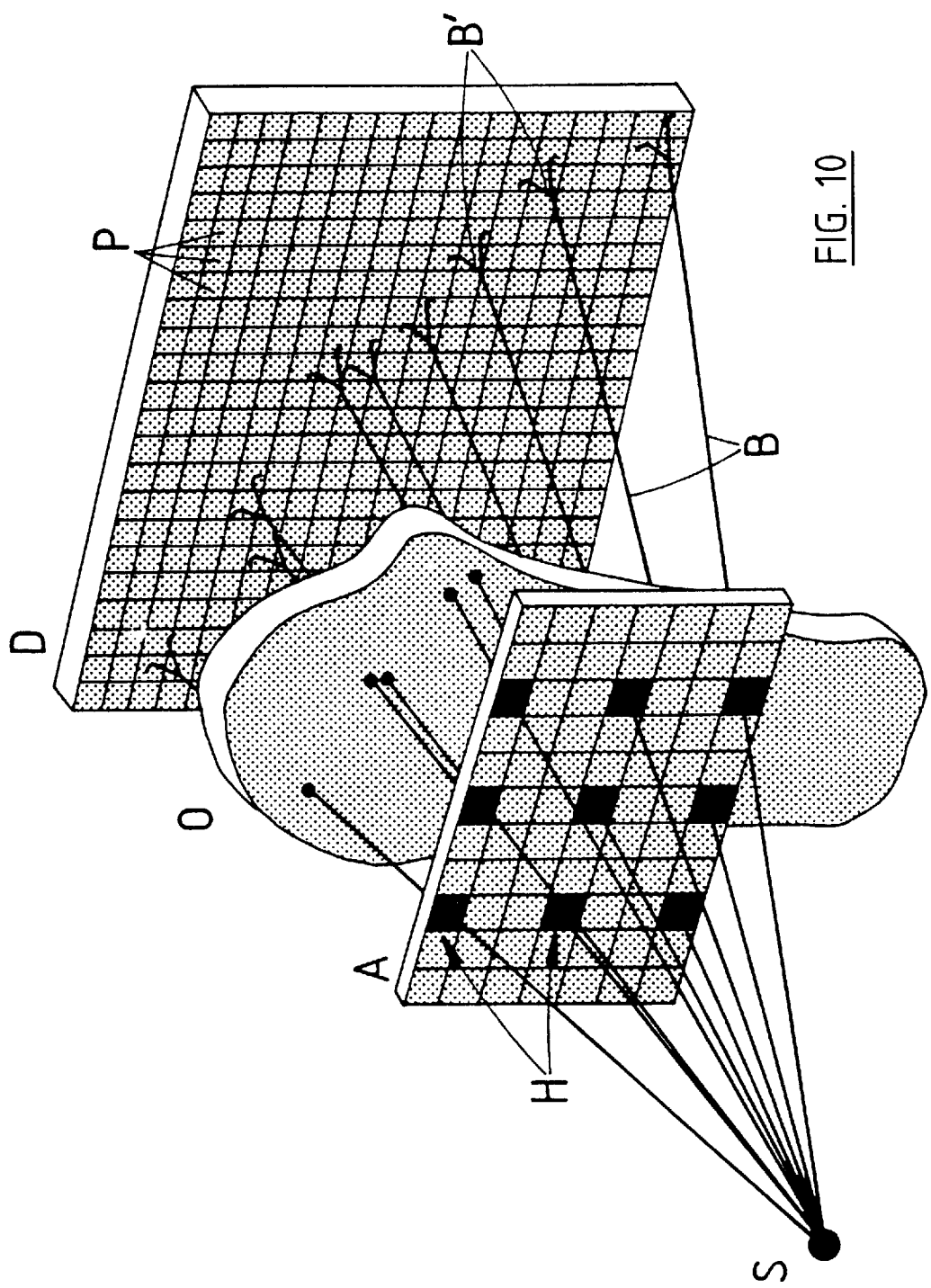
FIG. 10 is a three-dimensional view of apparatus similar to that of FIG. 9.
Figure 12A:
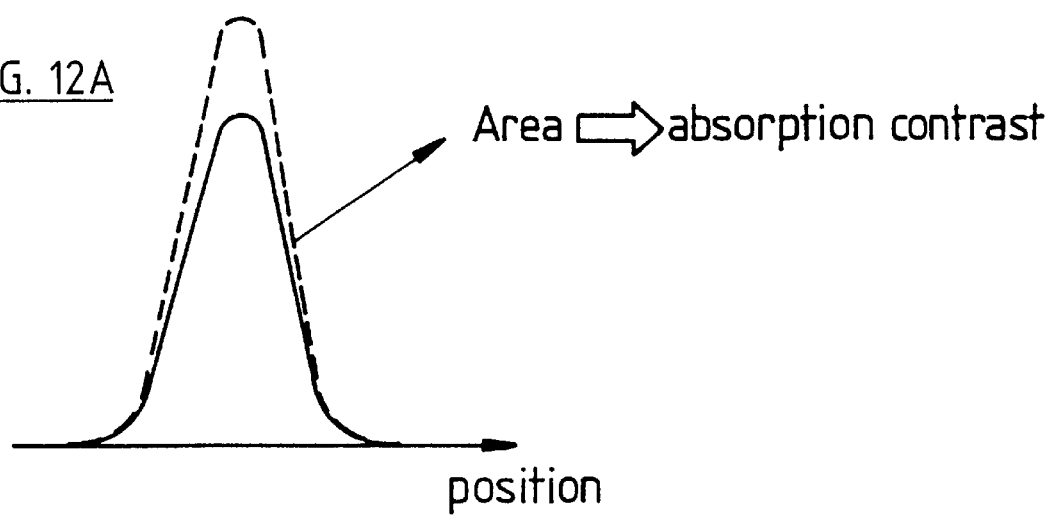
FIG. 12A–12C are diagrams explaining the location of different information in the detected spots.
Figure 12B:
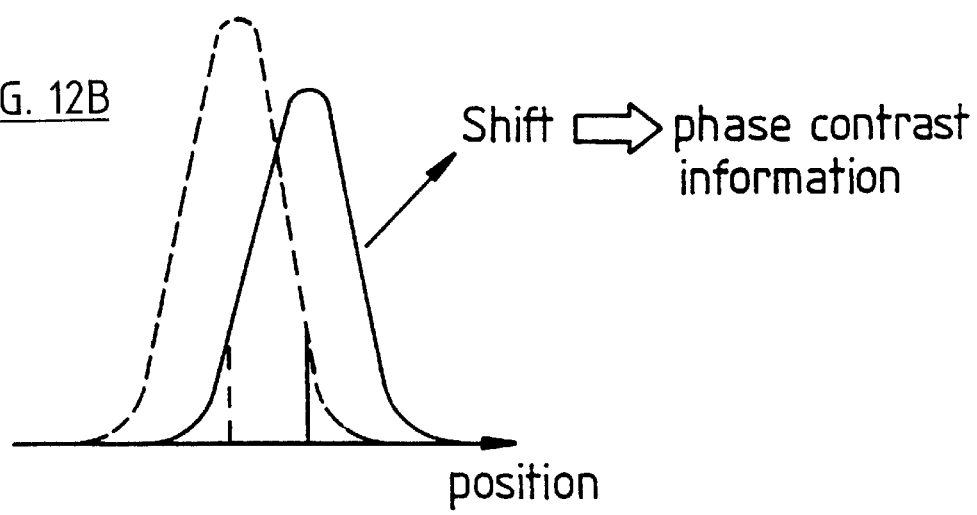
Figure 12C:
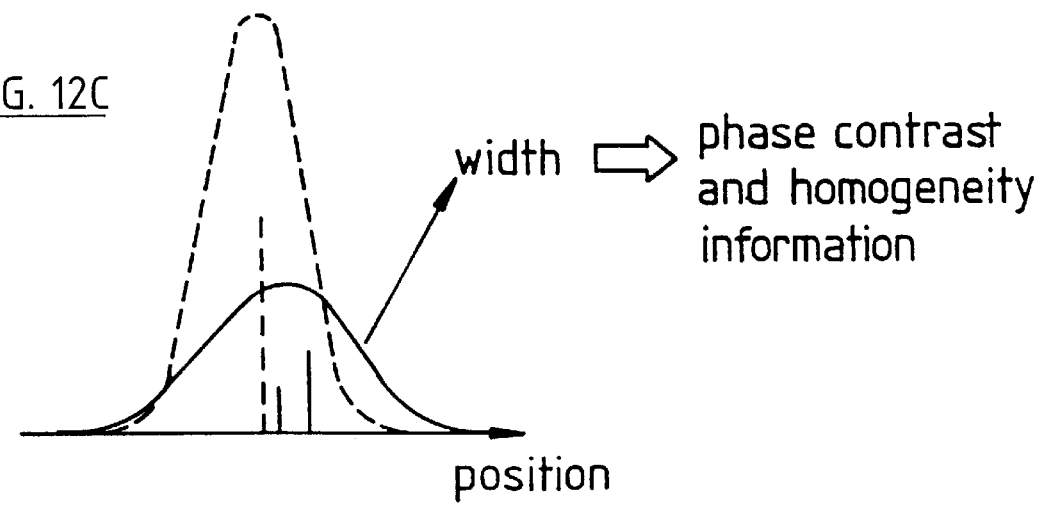

For concave lens structures of various elements, the angular deviation is given in the aforesaid Yang reference in units of μm/m as a function of x-ray photon) energy for a variety of materials. For x-rays of energies of 8 keV or more the effects of refraction of x-rays by different materials described above are extremely small and typically lead to angular deviations of a few arcsecs or less. In the case of the difference between protein and water, at 8 keV, the angular deviation due to a 45 degree boundary is of order 0.2 arcsec. Even such small effects may be measurable provided high spatial resolution 2-dimensional x-ray detectors and large distances between object and detector are used. The effect which it is sought to measure in order to build up a phase-contrast image is the determination of the small angular shifts in peak position induced by the object. Provided the spacing between holes (H) is chosen sufficiently large that neighbouring peaks at the detector (D) are well separated, then for sufficient spatial resolution at the detector, simultaneous absorption and phase contrast images at very high spatial resolution can be measured (FIG. 10). Essentially, absorption contrast information comes from the integrated intensity under the peak while the phase contrast information comes from the shift, $\Delta x_D$, in the peak position (FIGS. 12(*a*) and 12(*b*) respectively). In addition, information on the homogeneity of the object can be obtained from the peak width (FIG. 12(*c*)) while the effects of scattering can be reduced by background subtraction under the peak. The latter possibility offers potential improvements in conventional absorption radiography via reduced scatter and higher spatial resolution.

In the case of biological imaging, enhanced contrast in conventional absorption contrast radiography is often achieved by the use of high atomic number (Z) contrast agents. Such agents would also typically lead to increase in magnitude of peak shifts associated with phase-contrast imaging since the real part of the refractive index is also essentially proportional to Z (see Equation (1)).

For soft x-rays (less than say 8 keV), the refraction effects become stronger as $\lambda^2$ but penetration depth becomes less since absorption varies roughly as $\lambda^3$. Nonetheless, useful applications of the present type of image with soft x-rays may exist in the study of thin soft tissue samples such as for histology and pathology. A complicating factor is that such studies would probably require to be carried out in vacuum.

High spatial resolution 2-dimensional x-ray detectors based on CCDs and other TV systems have become commercially available with pixel sizes down to 5 μm and array sizes of 4096×4096. For the present purpose, high positional stability in readout is of highly desirable importance. Given such stability, it is possible in principle to determine peak shifts to much less than the size of a pixel by invoking (prior) knowledge of peak shapes. Such techniques are already used in optical astronomy to locate individual photons detected by an instrument. It would thus seem plausible that peak shifts could be measured to 0.1 or even 0.01 of a pixel width if peak shape is sufficiently well-defined. For example, a technique employing location of peak centroids to achieve a resolution of 0.01 of a pixel is to be found in Fillard et al, Optical Engineering, Nov 1993, Vol. 32, No. 11, p. 2936.

Arrays of interlaced CCDs with very little edge effect are also becoming available so that large banks of CCDs could be constructed and operated in parallel for large area x-ray imaging. Absolute stability of the CCD structures is not as important for the present purposes as internal relative stability of pixel positions which is extremely high for CCD detectors. Software may be used to overcome effects of any absolute position shifts of the CCD arrays.

As an illustration of the sort of magnitudes involved in designing a combined absorption and phase contrast image of the above type, the following sets of parameters are provided, again with reference to FIG. 11 and to Equation (2) above:

| Case 1 | |
| --- | --- |
| Source size ($d_s$) | 10 μm |
| Aperture size at A ($d_A$) | 10 μm |
| Angular shift due to refraction | Δθ = 1 arcsec (say) |
| $l_S = l_D = 1m$ (say) | |
| Then from Equation (2): | |
| Resulting spot size on the detector | $q_D = 30$ μm |
| Refraction effect (displacement of peak at the detector) | $\Delta x_D = 5$ μml |
| Case 2 | |
| Source size ($d_s$) | 10 μm |
| Aperture size at A ($d_A$) | 5 μm |
| Angular shift due to refraction | Δθ = 1 arcsec (say) |
| $l_s = 2m$ | |
| $l_D = 5$ m (say) | |
| Then from Equation (2): | |
| Resulting spot size on the detector | $q_D = 40$ μm |
| Refraction effect | $\Delta x_D = 24$ μm |
| Case 3 | |
| Source size ($d_s$) | 50 μm |
| Aperture size at A($d_A$) | 1 μm |
| Angular shift due to refraction | Δθ = 1 arcsec (say) |
| $l_S = 30$ m (say) | |
| $l_D = 10$ m (say) | |
| Then from Equation (2): | |
| Resulting spot size on the detector | $q_D = 18$ μm |
| Refraction effect | $\Delta x_D = 50$ μm |

It will be noted that the method and apparatus disclosed in connection with the second aspect of the invention, with reference to FIGS. 9 to 12, has the capability to simultaneously image a large object at high spatial resolution and does not rely on x-ray focusing devices or crystal optics.

Figure 13:
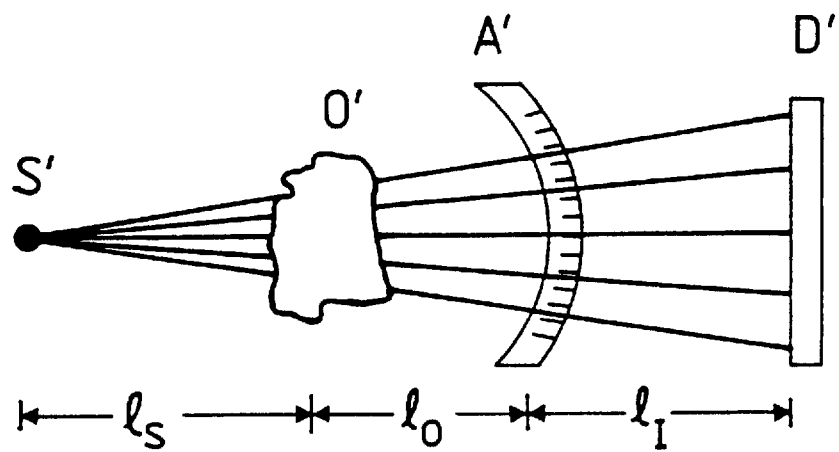
FIGS. 13 and 14 depict, in simple diagrammatic form, alternative embodiments of the second aspect of the invention.
Figure 14:
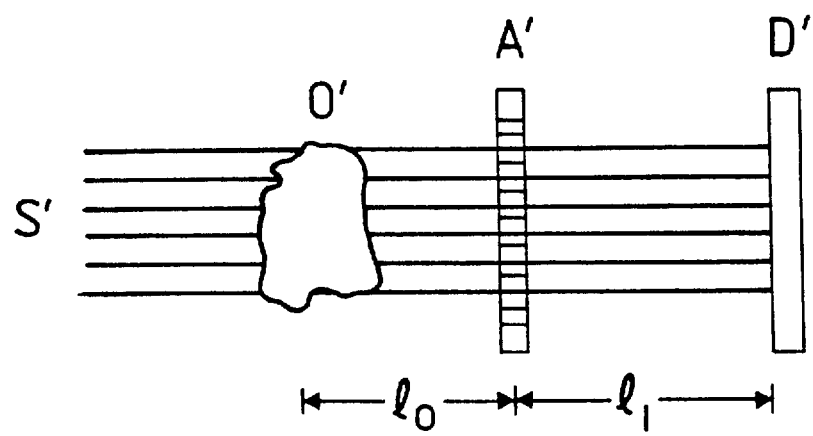

Alternative embodiments of the second aspect of the invention are illustrated in FIGS. 13 and 14. FIG. 13 depicts the case of a point source S' and FIG. 14 that of a synchrotron or other plane-wave source S". In these configurations, a microchannel-plate-type collimator A' is accurately aligned so as to allow radiation emanating from the source S' to be essentially transmitted by the collimator. With a point source (FIG. 3), this collimator is spherically curved as illustrated. For radiation which is slightly deviated in angle due to scattering or refraction in the sample, the microchannel plate collimator is such as to act as an efficient absorber. The radiation transmitted through the microchannel plate collimator leads to the formation of a bright-field image in this case. Typical dimensions for the absorbing collimator would be a channel radius of order 5 micrometers at 200 mm from the object O', leading again to a rejection of radiation scattered or refracted by more than a few arcsec or so, which is typical of refraction effects for samples envisaged and radiation around 20 keV. The pores of the microchannel plate may be of any cross-section and in fact should preferably be chosen so as to lead to the minimum possible degree of focusing effects.

Dark-field contrast images could be obtained by rotating the assembly of collimator A' around, say, the object or sample O', about an axis lying in the plane perpendicular to the optical axis and by amounts corresponding to the refraction effects in the sample (typically of the order of a few arcsecs for hard x-rays). An alternative is to translate the microchannel plate A' along the optic axis. A further alternative approach is to introduce a triangular prism of highly uniform material to cause a small angular deviation in the beam after object O', in the same way as a triangular prism is used in conventional light optics. Such an approach is probably simpler to operate in practice. The prism could be rotated about the optic axis. Alternatively, a lens-shaped x-ray refracting element may be introduced to produce radially symmetric angular deviations in the beam after the object and so allow the microchannel plate A' to remain at fixed orientation.

For the case of parallel illumination depicted in FIG. 14 the length of the microchannel plate collimator with 10 micrometer channel size required to produce a 5 arcsec angular selectivity might be of order 400 mm.

The present detailed discussion has been for the case of x-rays. As is well understood by those skilled in the art, similar classes of optical devices and configurations suited to neutron imaging are possible, making proper allowance for the different theory for scattering of neutrons and the differences in magnitudes and signs of the deviations of the refractive indices of neutrons from unity for different materials.

Throughout this specification and the claims which follows, unless the context requires otherwise, the word "comprise", or variations such as "comprises" or "comprising", will be understood to imply the inclusion of a stated integer or group of integers but not the exclusion of any other integer or group of integers.

I claim:

1. An x-ray or neutron optic configuration comprising:
a plurality of single crystal portions formed with respective spaced x-ray or neutron reflection faces formed at predetermined asymmetry angles to a Bragg diffraction plane in the respective crystal portion; and
means interconnecting said crystal portions whereby to maintain a first and second of said faces spaced apart for receipt of a sample therebetween and to allow small adjustments of the relative angle of said faces about the normal to the plane of diffraction while maintaining the normals to the Bragg planes for said first and second faces substantially in the plane of diffraction;
wherein said first face is arranged to be a monochromator and collimator with respect to x-rays or neutrons of appropriate wavelength incident on said first face and reflected thereby through the sample for receipt by the second face, said second face thereby serving as an analyzer face.

2. An x-ray or neutron beam optic configuration according to claim 1 wherein said single crystal portions are respective segments of a monolithic perfect or near-perfect single crystal shaped by initial growth or subsequent modification to define the respective reflection faces, which crystal thereby comprises said interconnecting means, and wherein said reflection faces are formed at predetermined asymmetry angles to a common Bragg diffraction plane in the crystal.

3. An x-ray or neutron beam optical configuration according to claim 2 wherein the additional face(s) are defined by said perfect or near perfect single crystal.

4. An x-ray or neutron beam optical configuration according to claim 2 wherein said monolithic crystal is cut to provide a base and integral upstanding lands, e.g. pillars, providing the respective x-ray reflection faces.

5. An x-ray or neutron beam optic configuration according to claim 1 wherein said single crystal portions are discrete crystals secured to structure which comprises said interconnecting means.

6. An x-ray or neutron beam optic configuration according to claim 5 wherein said discrete crystals have been cut from an original common crystal.

7. An x-ray or neutron beam optic configuration according to claim 1 wherein said interconnecting means allows maintenance and/or selection of an angular setting of the second face which is well matched in angular acceptance to the angular divergence of the beam from the first face or which is of higher angular resolution.

8. An x-ray or neutron beam optic configuration according to claim 1 wherein the interconnecting means is adapted to effect fine tuning and/or detuning of the relative angles of said first and second faces.

9. An x-ray or neutron beam optic configuration according to claim 1 wherein said first face is one of two or more reflective faces not necessarily having the same Bragg plane and which act to monochromate and collimate the beam incident on the sample.

10. An x-ray or neutron beam optic configuration according to claim 1 wherein said interconnecting means includes flexure means for effecting fine adjustment of the relative angles between said faces.

11. An x-ray or neutron beam optic configuration according to claim 9 wherein said flexure effecting means includes a reduced cross-section neck or web and associated positional transducer means.

12. An x-ray or neutron beam optical configuration according to claim 1 further including an imaging detector, preferably a two-dimensional imaging detector.

13. An x-ray or neutron beam optical configuration according to claim 1 further including a source of x-ray radiation arranged to direct a beam of x-rays onto said first face.

14. An x-ray or neutron beam optical configuration according to claim 13 wherein said source includes means to restrict the cross-section and of the beam and to enhance the angular collimation and intensity of the beam.

15. An x-ray or neutron beam optical configuration according to claim 1 further including one or more additional reflection faces with diffraction planes substantially parallel to the second face so as to enhance contrast and/or to magnify the beam coming from the sample.

16. An x-ray or neutron beam optic configuration comprising:
   a plurality of single crystal portions formed with respective spaced x-ray or neutron reflection faces formed at predetermined asymmetry angles to a Bragg diffraction plane in the respective crystal portion;
   means to mount a sample between a first and a second of said faces, which first face is arranged to be a monochromator and collimator with respect to x-rays or neutrons of appropriate wavelength incident on said first face and reflected thereby through the sample for receipt by the second face, said second face thereby serving as an analyzer face; and
   means interconnecting said crystal portions whereby to allow small adjustments of the relative angle of said faces about the normal to the plane of diffraction while maintaining the normals to the Bragg planes for said first and second faces substantially in the plane of diffraction.

17. A method of deriving an x-ray or neutron beam image signal of a sample comprising:
   directing an x-ray or neutron beam onto a first x-ray or neutron reflection face for reflection from that face through the sample to a second x-ray or neutron reflection face and thence to x-ray detection means,
   said reflection faces being interconnected such that a beam Bragg diffracted by the first face is at or near the correct angle for Bragg diffraction by the second face,
   said reflection faces being formed in respective single crystal portions at predetermined asymmetry angles to a Bragg diffraction plane in the respective crystal portion, wherein said first face is arranged to be a monochromator and collimator with respect to x-rays or neutrons of appropriate wavelength incident on said first face and reflected thereby through the sample for receipt by the second face, said second face thereby serving as an analyzer face; and
   said reflection faces being inter-connected so as to allow small adjustments of the relative angle of said reflection faces about the normal to the plane of diffraction while maintaining the normals to the Bragg planes for said first and second reflection faces substantially in the plane of diffraction.

18. A method of deriving an x-ray or neutron beam image signal of a sample comprising:
   directing an x-ray or neutron beam onto a first x-ray or neutron reflection face for reflection from that face through the sample to a second x-ray or neutron reflection face and thence to x-ray detection means,
   said reflection faces being interconnected such that a beam Bragg diffracted by the first face is at or near the correct angle for Bragg diffraction by the second face,
   said reflection faces being formed in respective single crystal portions at predetermined asymmetry angles to a Bragg diffraction plane in the respective crystal portion, wherein said first face is arranged to be a monochromator and collimator with respect to x-rays or neutrons of appropriate wavelength incident on said first face and reflected thereby through the sample for receipt by the second face said second face thereby serving as an analyzer face; and
   wherein the second face is well matched in angular acceptance to the angular divergence of the beam from the first face, or is of higher angular resolution.

19. A method of deriving an x-ray or neutron beam image signal of a sample comprising:
   directing an x-ray or neutron beam onto a first x-ray or neutron reflection face for reflection from that face through the sample to a second x-ray or neutron reflection face and thence to x-ray detection means,
   said reflection faces being interconnected such that a beam Bragg diffracted by the first face is at or near the correct angle for Bragg diffraction by the second face,
   said reflection faces being formed in respective single crystal portions at predetermined asymmetry angles to a Bragg diffraction plane in the respective crystal portion, wherein said first face is arranged to be a monochromator and collimator with respect to x-rays or neutrons of appropriate wavelength incident on said first face and reflected thereby through the sample for receipt by the second face, said second face thereby serving as an analyzer face;
   wherein said single crystal portions are respective segments of a monolithic perfect or near-perfect single crystal shaped by initial growth or subsequent modification to define the respective reflection faces, which crystal thereby interconnects said crystal faces, and
   wherein said reflection faces are formed at predetermined asymmetry angles to a common Bragg diffraction plane in the crystal.

20. An x-ray or neutron optic configuration comprising:

a plurality of single crystal portions formed with respective spaced x-ray or neutron reflection faces formed at predetermined asymmetry angles to a Bragg diffraction plane in the respective crystal portion; and means to allow small adjustments of the relative angle of said faces about the normal to the plane of diffraction while maintaining the normals to the Bragg planes for said first and second faces substantially in the plane of diffraction;

wherein said means allows maintenance and/or selection of an angular setting of the second face which is well matched in angular acceptance to the angular divergence of the beam from the first face, or is of higher angular resolution.

21. A method of deriving an x-ray or neutron beam image signal of a sample comprising directing an x-ray or neutron beam onto a first x-ray or neutron reflection face for reflection from that face through the sample to a second x-ray or neutron reflection face and thence to x-ray detection means, said reflection faces being formed in respective single crystal portions at predetermined asymmetry angles to a Bragg diffraction plane in the respective crystal portion, and further including maintaining and/or selecting an angular setting of the second face which is well matched in angular acceptance to the angular divergence of the beam from the first face, or is of higher angular resolution.

* * * * *